(12) United States Patent
Hayakawa

(10) Patent No.: US 12,017,899 B2
(45) Date of Patent: Jun. 25, 2024

(54) CLEANING METHOD FOR STERILIZATION LINE AND STERILIZATION LINE

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 997 days.

(21) Appl. No.: 16/962,134

(22) PCT Filed: Feb. 1, 2019

(86) PCT No.: PCT/JP2019/003613
§ 371 (c)(1),
(2) Date: Jul. 14, 2020

(87) PCT Pub. No.: WO2019/151477
PCT Pub. Date: Aug. 8, 2019

(65) Prior Publication Data
US 2020/0391989 A1 Dec. 17, 2020

(30) Foreign Application Priority Data
Feb. 5, 2018 (JP) ................................ 2018-018662

(51) Int. Cl.
*B67C 3/00* (2006.01)
*B08B 9/032* (2006.01)
(Continued)

(52) U.S. Cl.
CPC .............. *B67C 3/004* (2013.01); *B67C 3/007* (2013.01); *B08B 9/0321* (2013.01);
(Continued)

(58) Field of Classification Search
CPC ....... B67C 3/004; B67C 3/007; B67C 7/0073; B67C 2003/228; B08B 9/0321; B08B 2230/01; B08B 9/0325; A61L 2/04
See application file for complete search history.

(56) References Cited

U.S. PATENT DOCUMENTS 6,502,590 B1 * 1/2003 DeBartolo ................ F28G 9/00
134/169 C
2014/0286822 A1 9/2014 Hayakawa
2018/0352823 A1 * 12/2018 Thorsen .................... A61L 2/07

FOREIGN PATENT DOCUMENTS

JP 2000-153245 A1 6/2000
JP 2003-267492 A1 9/2003
(Continued)

OTHER PUBLICATIONS

International Search Report and Written Opinion (Application No. PCT/JP2019/003613) dated Mar. 19, 2019.

*Primary Examiner* — Regina M Yoo
(74) *Attorney, Agent, or Firm* — BURR PATENT LAW, PLLC

(57) ABSTRACT

A sterilization line comprising upstream-side and downstream-side tanks for storing liquid which are connected by a conduit for transferring the liquid, holding tubes for sterilizing the liquid which are disposed in an intermediate section of the conduit, heating units for heating the liquid in stages which are disposed in a section of the conduit from the upstream-side tank to the holding tubes, and cooling units for cooling the product liquid in stages which are disposed in a section of the conduit from the holding tubes to the downstream-side tank. A swing bend is used to perform switching between a section of a liquid flow path located on the upstream side of multiple intermediate piping systems and a cleaning solution path for a cleaning-in-place operation and switching between a section of the liquid flow (Continued)

path located on the downstream side and the cleaning solution path for the cleaning-in-place operation.

3 Claims, 7 Drawing Sheets

(51) Int. Cl.
*B67C 3/22* (2006.01)
*B67C 7/00* (2006.01)

(52) U.S. Cl.
CPC ..... *B08B 2230/01* (2013.01); *B67C 2003/228* (2013.01); *B67C 7/0073* (2013.01)

(56) References Cited

FOREIGN PATENT DOCUMENTS

| | | |
|---|---|---|
| JP | 2007-022600 A1 | 2/2007 |
| JP | 2007-331801 A1 | 12/2007 |
| JP | 2013-091018 A1 | 5/2013 |
| JP | 2017-056958 A1 | 3/2017 |

* cited by examiner

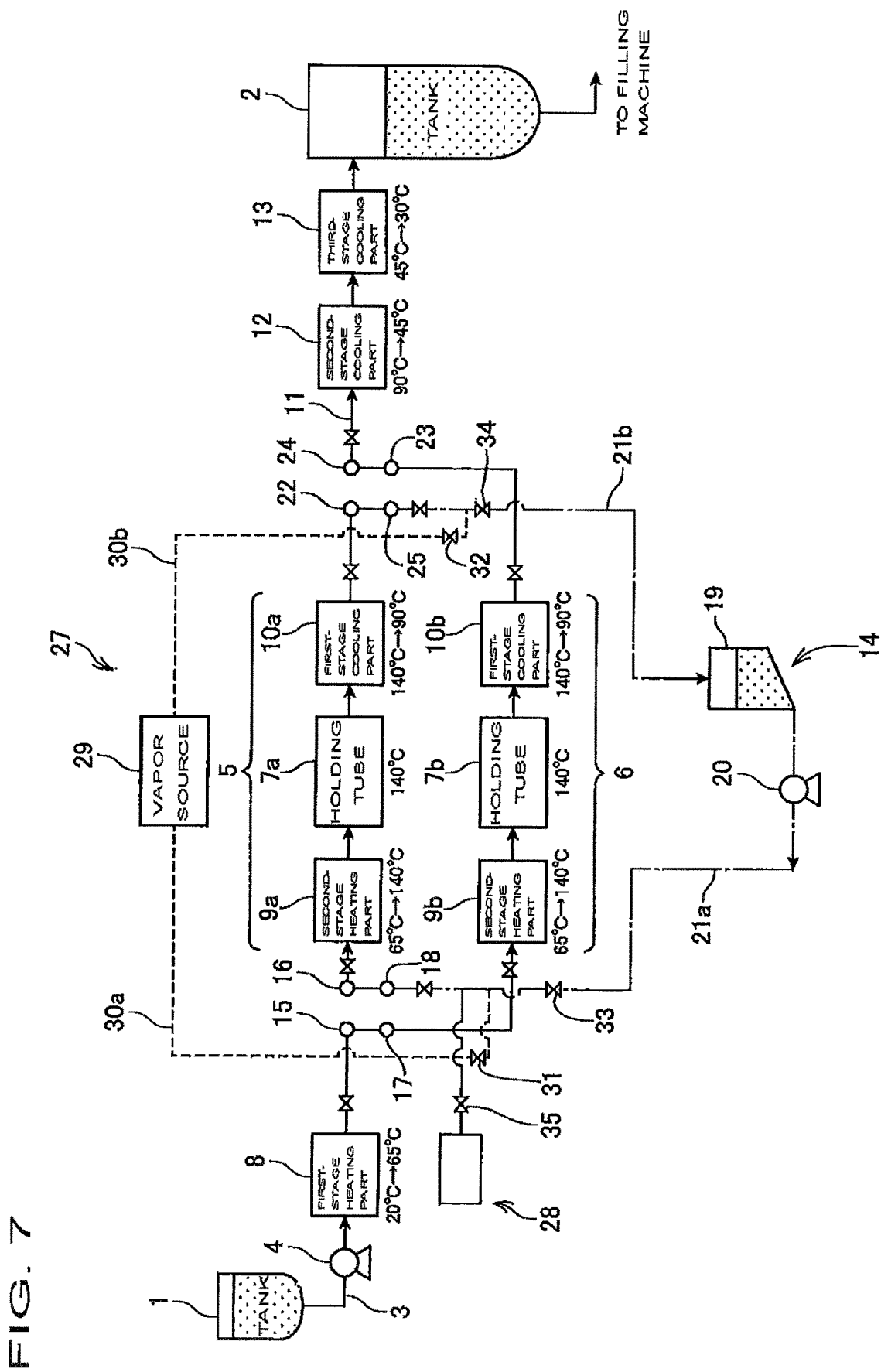

CLEANING METHOD FOR STERILIZATION LINE AND STERILIZATION LINE

TECHNICAL FIELD

The present invention relates to a cleaning method for a sterilization line that sterilizes a product liquid such as a drink in an aseptic filling machine that aseptically fills a container with a drink, and the sterilization line.

BACKGROUND ART

Conventionally, before an aseptic filling machine for a drink or the like starts filling a container such as a bottle with a drink, a supply piping system for the drink or the like is subjected to Cleaning in Place (CIP) for removing impurities and bacteria from the inside of the piping system and Sterilization in Place (SIP) for sterilizing the interior of the supply piping system (see Patent Literature 1).

The CIP is performed by circulating a mixture of water and an alkali cleaning agent such as caustic soda or an acidic cleaning agent as an additive in the supply piping system, for example. The CIP removes impurities such as drink residues on the inside of the supply piping system (see Patent Literatures 1, 2, and 3).

The SIP is performed by circulating heated steam, hot water or the like in the supply piping system cleaned by the CIP, for example. The SIP sterilizes the interior of the supply piping system and makes it aseptic (see Patent Literature 1).

The supply piping system of an aseptic filling system that handles a large amount of product liquid is provided with a sterilization line. The sterilization line includes an upstream-side tank that stores a prepared product liquid such as a drink and a downstream-side tank that stores the product liquid having been sterilized and supplies the product liquid to a filling machine. The upstream-side tank and the downstream-side tank are connected to each other by a conduit through which the product liquid is transferred. The conduit is provided, in a middle section thereof, with a holding tube that sterilizes the product liquid. The conduit is provided, in a part thereof between the upstream-side tank and the holding tube, two stages of heating parts that heat the product liquid in a stepwise manner. The conduit is provided, in a part thereof between the holding tube and the downstream-side tank, three stages of cooling parts that cool the product liquid in a stepwise manner. Since pluralities of stages of heating parts and cooling parts are provided, even a large amount of product liquid can be properly and smoothly heated to a sterilization temperature and smoothly cooled to room temperature.

In general, when the filling machine fills a container such as a PET bottle with the product liquid, the product liquid fed under pressure through the conduit from the upstream-side tank to the downstream-side tank is heated from room temperature to about 65° C. in a first-stage heating part, further heated from about 65° C. to about 140° C. in a second-stage heating part, heated and maintained at about 140° C. for about 30 to 60 seconds and thus sterilized in the holding tube, then cooled from about 140° C. to about 90° C. in a first-stage cooling part, further cooled from about 90° C. to about 45° C. in a second-stage cooling part, and further cooled from about 45° C. to about 30° C. in a third-stage cooling part. The downstream-side tank stores the product liquid at 30° C. coming from the third-stage cooling part. The product liquid is fed from the downstream-side tank to the filling machine, and the filling machine fills a large number of containers such as PET bottles with the product liquid while the containers are traveling at high speed.

With regard to the sterilization line described above, there has been proposed a method of reducing the time required to start production of the next product liquid by providing a similar piping system in parallel with the piping system from the second-stage heating part to the first-stage cooling part, which lies in a temperature range in which the product liquid can be burned, and completing the CIP and the SIP for one piping system while the other piping system is used to feed the product liquid (see Patent Literature 4).

CITATION LIST

Patent Literature

Patent Literature 1: Japanese Patent Laid-Open No. 2007-22600
Patent Literature 2: Japanese Patent Laid-Open No. 2007-331801
Patent Literature 3: Japanese Patent Laid-Open No. 2000-153245
Patent Literature 4: Japanese Patent Laid-Open No. 2013-91018

SUMMARY OF INVENTION

Technical Problem

With the conventional sterilization line for a product liquid, sterilization of the product liquid and the CIP and other processes can be performed in parallel by alternately switching between two piping systems, and therefore, the efficiency of production of product liquid packages can be improved.

However, the piping system described above requires a large installation space and is expensive. Therefore, if the sterilization line has two rows of such piping systems, the sterilization line is large and extremely expensive. In addition, the CIP, the SIP, and other processes require a long time, an increased amount of agents, and a large amount of energy.

In view of this, as described in Patent Literature 4, it is proposed that the time required to start production of the next product liquid is reduced by multiplexing only the heating part and the cooling part in the sterilization line that lie in a temperature range in which the product liquid can be burned and performing the CIP and the SIP for the line that is not being used. In Patent Literature 4, when starting production of the next product liquid, the flow path is changed by a valve operation. However, in order to switch between the parallel flow paths for feeding the product liquid, the cleaning solution for the CIP and the heated fluid for the SIP with the valve operation, a complicated valve arrangement is needed, and the capital investment increases as the number of valves increases. In addition, there is a risk that the product liquid is mixed with the cleaning solution or the like because of a valve operation error, remaining of the liquid, a damage to the valve or a leakage from the valve. There is a demand for a cleaning method that is safe and has high productivity that can reduce the time required for the CIP for removing any burned product liquid from a sterilization line and prevent the product liquid from being mixed with a fluid other than the product liquid such as a cleaning solution.

An object of the present invention is to provide a cleaning method for a sterilization line and the sterilization line that can solve the problems described above.

Solution to Problem

A cleaning method for a sterilization line according to the present invention is a cleaning method for a sterilization line, the sterilization line including a conduit through which a product liquid is transferred, the conduit being provided with one or more stages of heating parts that sterilize the product liquid and one or more stages of cooling parts that cool the product liquid from the heating parts in a stepwise manner, the sterilization line including a plurality of parallel intermediate piping systems in a section thereof between a stage of a heating part that lies in a temperature range in which the product liquid can be burned and a stage of a cooling part that lies in a temperature range in which the product liquid can be burned, the section including at least the stage of a heating part that lies in a temperature range in which the product liquid can be burned, and CIP of the plurality of parallel intermediate piping systems being performed by switching between the intermediate piping systems, wherein switching between a flow path of the product liquid and a flow path of a cleaning solution used for the CIP upstream of the plurality of intermediate piping systems and switching between the flow path of the product liquid and the flow path of the cleaning solution used for the CIP downstream of the plurality of intermediate piping systems are achieved by a swing bend.

In the cleaning method for a sterilization line according to the present invention, preferably, an intermediate piping system is subjected to SIP after or at the same time as the CIP and is further subjected to a positive pressurization process.

In the cleaning method for a sterilization line according to the present invention, preferably, the swing bend is provided in a shielded chamber, an interior of the chamber is sterilized before the switching between flow paths, and the switching between flow paths is performed while maintaining an aseptic condition in the sterilized chamber.

A sterilization line according to the present invention is a sterilization line comprising: a connecting conduit through which a product liquid is transferred; one or more stages of heating parts that are provided in a middle section of the conduit and sterilize the product liquid; and one or more stages of cooling parts that cool the product liquid from the heating parts in a stepwise manner, the sterilization line further comprising a plurality of parallel intermediate piping systems in a section thereof between a stage of a heating part that lies in a temperature range in which the product liquid can be burned and a stage of a cooling part that lies in a temperature range in which the product liquid can be burned, the section including at least the stage of a heating part that lies in a temperature range in which the product liquid can be burned, the intermediate piping systems being provided with a CIP unit that cleans the intermediate piping systems, and a sterilization process for the product liquid in the intermediate piping system and CIP of the intermediate piping system being performed by switching between the plurality of parallel intermediate piping systems, wherein a swing bend is provided to achieve switching between a flow path of the product liquid and a flow path of a cleaning solution used for the CIP upstream of the plurality of intermediate piping systems and switching between the flow path of the product liquid and the flow path of the cleaning solution used for the CIP downstream of the plurality of intermediate piping systems.

In the sterilization line according to the present invention, preferably, the intermediate piping systems are provided with a SIP unit that performs SIP that sterilizes an interior of the intermediate piping systems after or at the same time as the CIP of the interior of the intermediate piping systems and a positive pressurization unit that keeps the interior of the intermediate piping systems at a positive pressure after the SIP.

In the sterilization line according to the present invention, preferably, the swing bend is provided in a shielded chamber, and the sterilization line is provided with a sterilization unit that sterilizes an interior of the chamber.

Advantageous Effects of Invention

According to the present invention, since the sterilization line has a plurality of parallel intermediate piping systems only in a section thereof in which the product liquid is likely to be burned, the sterilization line can be smaller and simpler and therefore more economical than a sterilization line that is totally parallel. Since only the intermediate piping system in which the product is burned needs to be subjected to the CIP, or the CIP, the SIP, and the positive pressurization process, the amount of cleaning-solution or sterilization fluid can be reduced, and the running cost can be reduced. Furthermore, although piping is changed in order to alternately perform the sterilization process for the product liquid and the CIP for the intermediate piping system, the switching between the plurality of parallel intermediate piping systems is achieved with a swing bend, so that the valve arrangement is simplified, and the capital investment can be reduced. Furthermore, the product liquid can be prevented from being mixed with the cleaning solution or the like because of a valve operation error, remaining of the cleaning solution, a damage to a valve or a leakage from a valve. After sterilization of the product liquid, the flow path is changed with the swing bend to couple the intermediate piping system having been used for sterilization of the product liquid to the CIP unit and perform the CIP of the part where the product liquid is burned. The intermediate piping system having been used for sterilization of the product liquid may be subjected to the SIP after or at the same time as the CIP. On the other hand, the other intermediate piping system having been subjected to the CIP or the CIP and SIP is coupled to the upstream-side conduit in which the product liquid flows, and is subjected to the CIP for washing away any product liquid remaining in the piping. Since the part in which the product liquid can be burned is already cleaned when the product liquid is sterilized, the CIP for washing away the remaining product liquid ends in a short time and therefore is economical. Furthermore, since the swing bend is provided in a chamber that can be sterilized, the intermediate piping system that is not in use can enter into the standby state after the intermediate piping system is subjected to the CIP, the SIP and the positive pressurization process. As a result, the time required for the CIP or the like can be reduced when changing the product liquid, so that the productivity can be improved. In addition, the safety can be ensured since the swing bend is used to switch between the piping systems.

Furthermore, the intermediate piping system that is not in use can be subjected to CIP while the other intermediate piping system is sterilizing the product liquid or is being subjected to the CIP or SIP. Therefore, unlike the conventional technique, an expensive agent having a high cleaning effect does not need to be used in order to reduce the CIP time, or the cleaning solution used does not need to have high temperature or high concentration. An inexpensive agent having a relatively low cleaning effect can be used, and the cleaning can take a relatively long time.

BRIEF DESCRIPTION OF THE DRAWINGS

FIG. 7 is a block diagram showing the sterilization line according to the second embodiment of the present invention in which the interior of the one intermediate piping system is subjected to CIP, SIP, and the positive pressurization process while the other intermediate piping system is used to sterilize the product liquid.

DESCRIPTION OF EMBODIMENTS

In the following, embodiments of the present invention will be described with reference to the drawings.

First Embodiment

Figure 1:
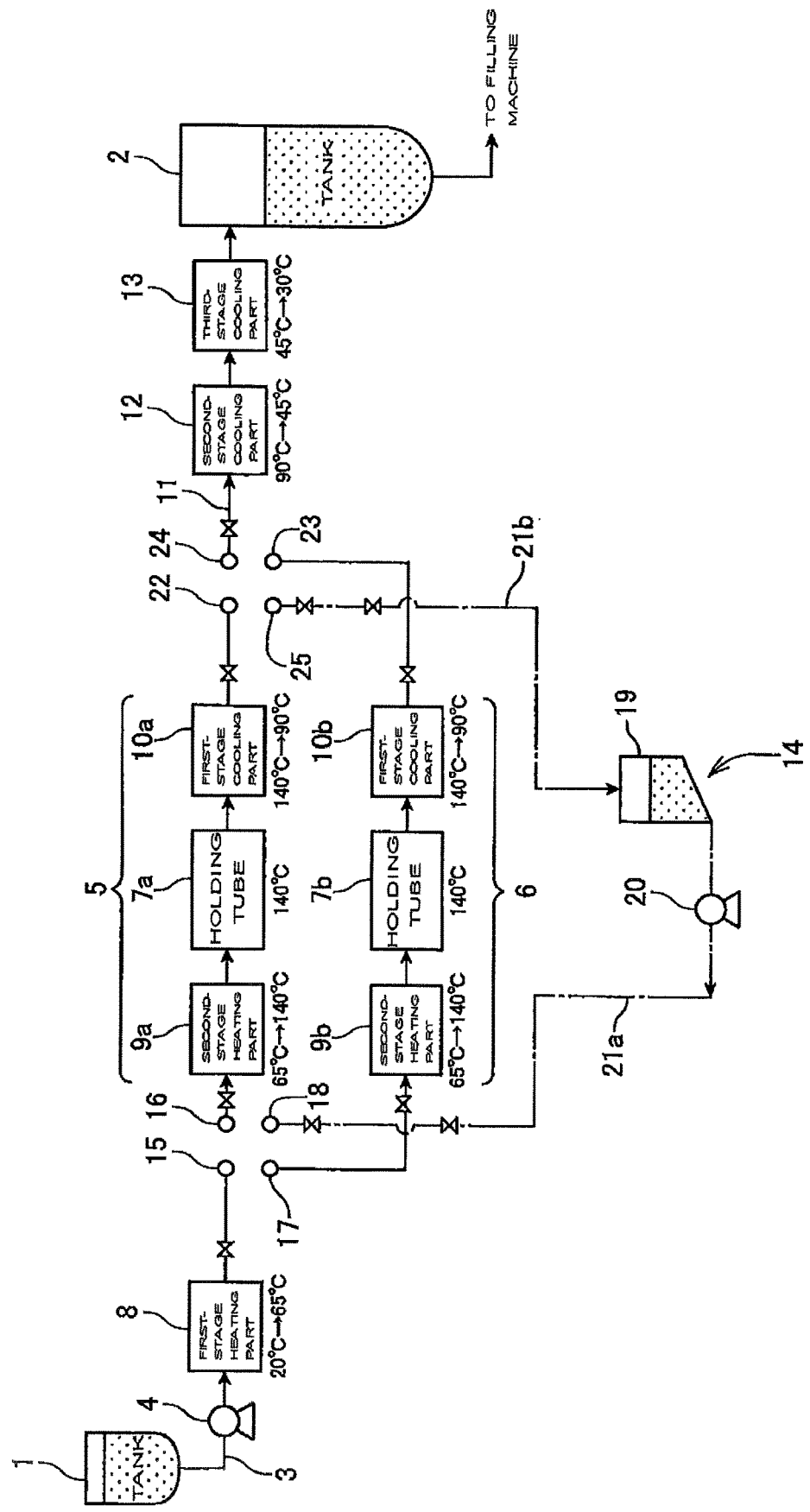
FIG. 1 is a block diagram showing a sterilization line according to a first embodiment of the present invention.

In a piping system of an aseptic filling machine that handles a large amount of product liquid such as a drink, a sterilization line such as one shown in FIG. 1 is provided.

In FIG. 1, reference numeral 1 denotes an upstream-side tank that stores a product liquid such as a drink that is prepared but is yet to be sterilized, and reference numeral 2 denotes a downstream-side tank that temporarily stores the product liquid sterilized and then supplies the product liquid to a filling machine (not shown).

The upstream-side tank 1 and the downstream-side tank 2 can each store a large amount of product liquid. For example, the upstream-side tank 1 and the downstream-side tank 2 each have a volume capable of storing several tons to a dozen tons of product liquid. The upstream-side tank 1 is configured to keep the temperature of the product liquid yet to be sterilized at room temperature, for example, about 20° C., and the downstream-side tank 2 is configured to keep the sterilized product liquid at room temperature, for example, about 30° C.

Although not shown, the filling machine is of a type that injects the sterilized product liquid into containers, such as sterilized PET bottles or sterilized paper containers assembled by quickly welding the sides and bottom thereof to each other, that are traveling at high speed at regular intervals around a horizontally arranged wheel by inserting nozzles traveling following the containers at high speed into the containers. When the containers are bottles, a capper is coupled to the filling machine. The capper is also configured to make the containers such as PET bottles filled with the product liquid travel at high speed at regular intervals around a similar wheel. The capper seals mouths of the containers filled with the product liquid with sterilized caps.

The upstream-side tank 1 and the downstream-side tank 2 are connected to each other by an upstream-side conduit 3 through which the product liquid is transferred. The upstream-side conduit 3 is provided with a pump 4 for feeding the product liquid under pressure at a location closer to the upstream-side tank 1.

A sterilization line for sterilizing the product liquid is provided downstream of the pump 4 provided on the upstream-side conduit 3. In a part where the product liquid can be burned during sterilization, a plurality of intermediate piping systems is provided in parallel. A first intermediate piping system 5 is provided with a holding tube 7a, and a second intermediate piping system 6 is provided with a holding tube 7b. The holding tubes 7a and 7b are shell-and-tube heat exchangers in which the product liquid flows in a long tube and is heated through the tube, for example. In the holding tubes 7a and 7b, the product liquid is heated to 140° C., for example. The product liquid takes 30 to 60 seconds to pass through the heat exchangers and is sterilized by being continuously heated at the temperature of 140° C. for the period.

In order to heat the product liquid in a stepwise manner, the upstream-side conduit 3 is provided with a first-stage heating part 8 at a location between the upstream-side tank 1 and the first intermediate piping system 5 or second intermediate piping system 6. The number of stages of heating parts can be changed as appropriate. By providing more than two stages, the raising of temperature from room temperature to a sterilization temperature can also be more finely divided.

The first intermediate piping system 5 and the second intermediate piping system 6 are provided with second-stage heating parts 9a and 9b, respectively, that further heat the product liquid heated by the first-stage heating part 8.

The first-stage heating part 8 is formed by a plurality of shell-and-tube heat exchangers coupled in series to each other and heats the product liquid fed under pressure from the upstream-side tank 1 by the pump 4 from 20° C. to 65° C. The second-stage heating parts 9a and 9b are each formed by more shell-and-tube heat exchangers than the first-stage heating part 8 coupled in series to each other and heat the product liquid fed from the first-stage heating part 8 from 65° C. to 140° C. The product liquid heated to 140° C. is fed to the holding tube 7a or 7b, kept at 140° C. in the holding tube 7a or 7b and then fed to the following cooling part.

The product liquid reaches the holding tube 7a or 7b after passing through a plurality of stages of heating parts, that is, the first-stage heating part 8 and the second-stage heating part 9a or 9b. Therefore, even if the product liquid flows at high speed, the product liquid is smoothly heated to high temperature.

The first intermediate piping system 5 is provided with a first-stage cooling part 10a at a location between the holding tube 7a and the downstream-side tank 2, and the second intermediate piping system 6 is provided with a first-stage cooling part 10b at a location between the holding tube 7b and the downstream-side tank 2. Furthermore, a downstream-side conduit 11 is provided with a second-stage cooling part 12 and a third-stage cooling part 13 in sequence. These cooling parts cool the product liquid in a stepwise manner. The number of stages of cooling parts can be changed as appropriate. By providing beyond three stages, the lowering of temperature from the sterilization temperature to room temperature can be more finely divided.

The first-stage cooling parts 10a and 10b are each formed by a plurality of shell-and-tube heat exchangers coupled in series to each other and cool the sterilized product liquid fed under pressure from the holding tubes 7a and 7b, respectively, by the pump 4 from 140° C. to 90° C. The second-stage cooling part 12 is formed by the same number of shell-and-tube heat exchangers as the first-stage cooling part 10a or 10b or less shell-and-tube heat exchangers than the first-stage cooling part 10a or 10b coupled in series to each other and cools the product liquid fed from the first-stage cooling part 10a or 10b from 90° C. to 45° C. The third-stage cooling part 13 is formed by the same number of shell-and-tube heat exchangers as the second-stage cooling part 12 or less shell-and-tube heat exchangers than the second-stage cooling part 12 coupled in series to each other and cools the product liquid fed from the second-stage cooling part 12 from 45° C. to 30° C. The product liquid cooled to 30° C. is fed to the downstream-side tank 2, and is further fed from the downstream-side tank 2 to the filling machine (not shown).

As described above, the product liquid is heated in the first-stage heating part 8 when flowing in the upstream-side conduit 3, and then flows to the first intermediate piping system 5 or second intermediate piping system 6 and is further heated in the second-stage heating part 9a or 9b in the intermediate piping system. The product liquid is then sterilized in the holding tube 7a or 7b by being kept at high temperature and then cooled in the first-stage cooling part 10a or 10b. The product liquid flows from the intermediate piping system to the downstream-side conduit 11 and then reaches the downstream-side tank 2 after passing through the second-stage cooling part 12 and the third-stage cooling part 13. Therefore, even if the product liquid flows at high speed, the product liquid can be smoothly cooled to room temperature.

The sterilized product liquid at room temperature having flowed into the downstream-side tank 2 is fed to the filling machine described above, and the filling machine fills a large number of sterilized containers such as PET bottles or paper containers traveling at high speed with the product liquid.

In the first embodiment, as shown in FIG. 1, in the sterilization line connecting the upstream-side tank 1 and the downstream-side tank 2 to each other, the first intermediate piping system 5 and the second intermediate piping system 6 are provided in parallel between the second-stage heating parts 9a and 9b and the first-stage cooling parts 10a and 10b. Depending on the degree of burning of the product, the first-stage cooling parts 10a and 10b may be omitted, and only the second-stage heating parts 9a and 9b, which use a heating medium such as vapor or hot water to heat the product liquid, or only the holding tubes 7a and 7b may be provided in parallel.

The product liquid is not burned in the piping system in a preset temperature range of the first-stage heating part 8, whereas the product liquid can be burned in a preset temperature range of the second-stage heating part 9a or 9b. Similarly, the product liquid can be burned in a preset temperature range of the first-stage cooling part 10a or 10b, whereas the product liquid is not burned in preset temperature ranges of the second-stage cooling part 12 and the third-stage cooling part 13. In this case, the temperature range in which the product liquid can be burned is equal to or higher than 60° C., at which proteins are denatured. However, in the first-stage heating part 8 and the second-stage cooling part 12, the flow velocity of the product liquid is high, and therefore the product liquid is not burned. Depending on the amount of the proteins contained in the product liquid, in general, the temperature range in which the product liquid can be burned is from 60° C. to 150° C.

As described above, the numbers of stages of the heating parts 8, 9a, 9b, 7a and 7b and the cooling parts 10a, 10b, 12 and 13 can be changed as required. In that case, the numbers of stages of the heating parts and the cooling parts in which the product liquid can be burned also change.

As shown in FIG. 1, the sterilization line is provided with a CIP unit 14 that performs CIP for the first intermediate piping system 5 and the second intermediate piping system 6. The CIP unit 14 is to clean the interiors of the second-stage heating parts 9a and 9b, the holding tubes 7a and 7b and the first-stage cooling parts 10a and 10b, in which the product liquid can be burned, by flowing a cleaning solution such as an acidic solution or alkali solution in the first intermediate piping system 5 or second intermediate piping system 6. The CIP unit 14 has a cleaning solution storage tank 19 in which the cleaning solution is input or stored, a cleaning solution pump 20 that feeds the cleaning solution under pressure, and cleaning solution inflow piping 21a and cleaning solution outflow piping 21b in which the cleaning solution is circulated. Although FIG. 1 shows the cleaning solution pump 20 as being provided on the cleaning solution inflow piping 21a, a cleaning solution pump may also be provided on the cleaning solution outflow piping 21b to flow the cleaning solution from downstream to upstream. If the cleaning solution is flowed from downstream to upstream, the pressure of the cleaning solution is exerted on a different part than when the cleaning solution is flowed from upstream to downstream, and thus the effect of the cleaning can be improved.

As shown in FIG. 1, the sterilization line has the piping ends described below in an upstream part thereof. That is, the upstream-side conduit 3 in which the product liquid from the upstream-side tank 1 flows has a product liquid inlet 15, the first intermediate piping system 5 has a first intermediate piping system inlet 16, the second intermediate piping system 6 has a second intermediate piping system inlet 17, and the CIP unit 14 has a cleaning solution inlet 18. The sterilization line has the piping ends described below in a downstream part thereof. That is, the first intermediate piping system 5 has a first intermediate piping system outlet 22, the second intermediate piping system 6 has a second intermediate piping system outlet 23, the downstream-side conduit 11 in which the product liquid flows to the downstream-side tank 2 has a product liquid outlet 24, and the CIP unit 14 has a cleaning solution outlet 25.

Piping ends are coupled to each other by a so-called swing bend. The swing bend is a unit that selectively connects open ends of a plurality of pipes arranged and fixed in parallel to each other at equal distances with a U-shaped or angled U-shaped pipe shaped to the distances. When switching between flow paths is achieved by a valve operation as described in Patent Literature 4, the product liquid can be mixed with the cleaning solution or the like because of a valve operation error, remaining of the solution, a damage to the valve or a leakage from the valve. However, such mixing can be prevented by using the swing bend to switch between flow paths.

Figure 4:
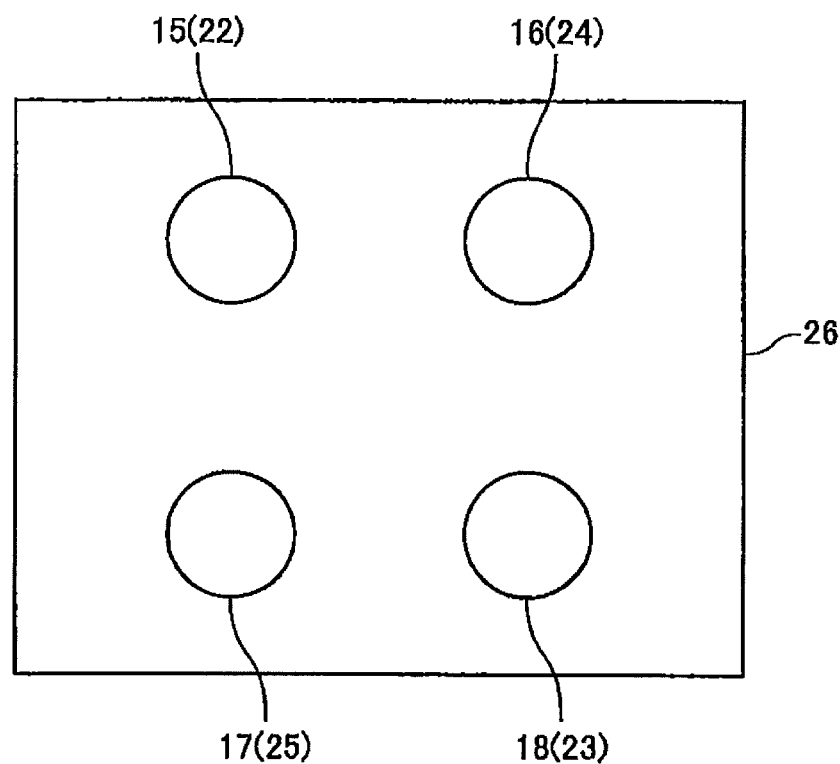
FIG. 4 shows a swing bend panel that switches between flow paths in sterilization lines according to embodiments of the present invention.

The piping ends are provided in a swing bend panel 26 as shown in FIG. 4. For example, two open ends provided in the swing bend panel 26 are coupled to each other by a U-shaped pipe. The coupling may be manually achieved. Alternatively, if two U-shaped pipes are connected to a shaft, which can be rotated by a rotational air actuator, in such a manner that the U-shaped pipes can be press-fitted to and separated from the openings of the swing bend panel 26 with an air motor, the flow path can be mechanically changed.

Figure 2:
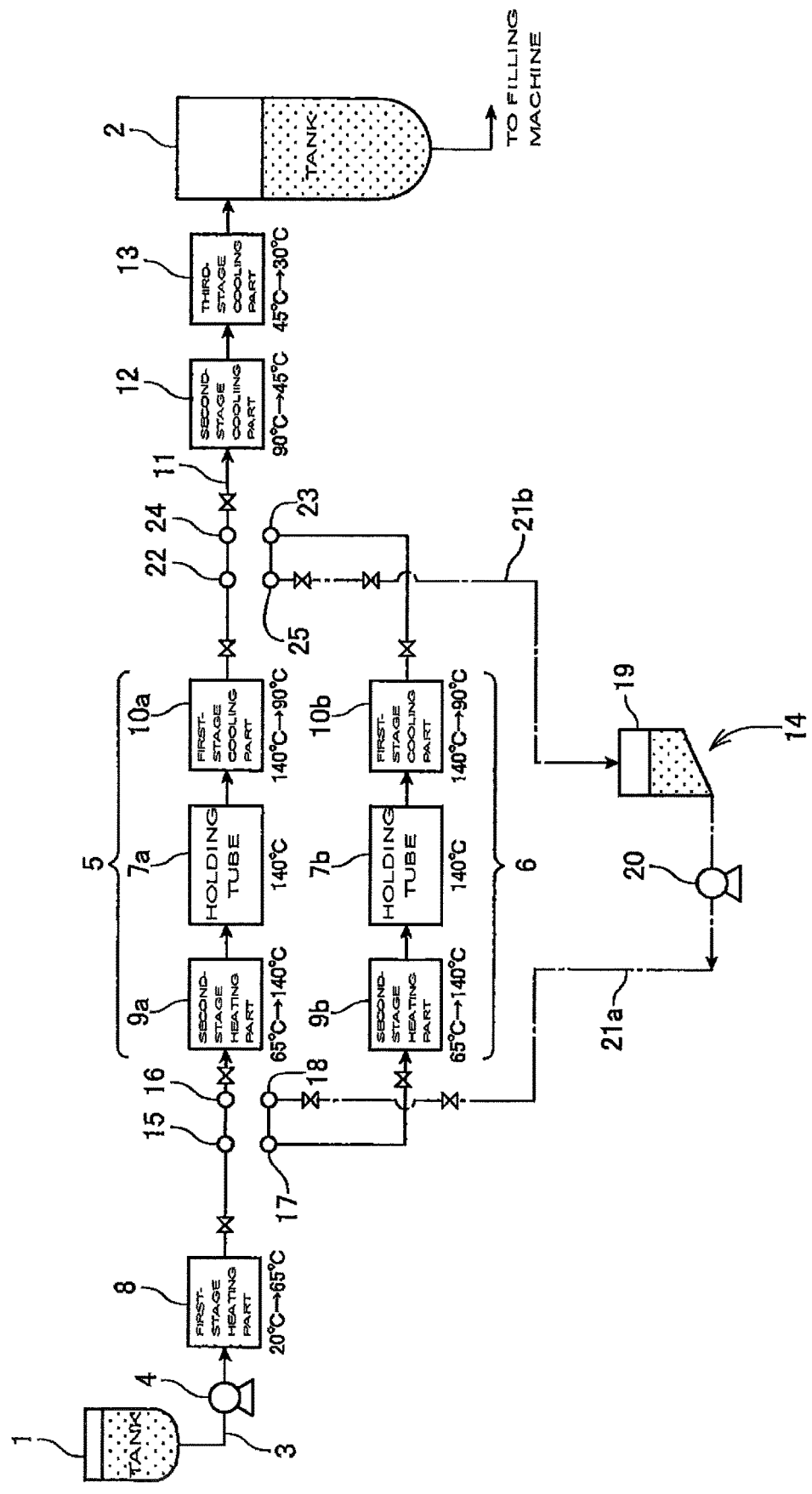
FIG. 2 is a block diagram showing the sterilization line according to the first embodiment of the present invention in which one intermediate piping system is used to sterilize a product liquid while the interior of the other intermediate piping system is subjected to CIP.

As shown in FIG. 2, when the product liquid inlet 15 and the first intermediate piping system inlet 16 are coupled to each other, the second intermediate piping system inlet 17 and the cleaning solution inlet 18 are coupled to each other, the first intermediate piping system outlet 22 and the product liquid outlet 24 are coupled to each other, and the second intermediate piping system outlet 23 and the cleaning solution outlet 25 are coupled to each other, the product liquid flows in the first intermediate piping system 5, and the cleaning solution flows in the second intermediate piping system 6.

The product liquid is supplied from the upstream-side tank 1 through the upstream-side conduit 3, and is fed under pressure to the first-stage heating part 8 by the pump 4. The product liquid is heated from room temperature to about 65° C. by the first-stage heating part 8. The product liquid is rarely burned in the first-stage heating part. The product liquid is fed to the first intermediate piping system 5 through the product liquid inlet 15 and the first intermediate piping system inlet 16, heated from 65° C. to about 140° C. in the second-stage heating part 9a, and sterilized in the holding tube 7a by being kept at about 140° C. The sterilized product liquid is cooled from about 140° C. to 90° C. in the first-stage cooling part 10a. The part in which the product liquid is most likely to be burned is the second-stage heating part 9a, and impurities derived from the product liquid can be deposited on the holding tube 7a and the first-stage cooling part 10a. The product liquid flows to the downstream-side conduit 11 through the first intermediate piping system outlet and the product liquid outlet 24 coupled to each other, cooled from about 90° C. to about 45° C. by the second-stage cooling part 12, further cooled from about 45° C. to about 30° C. by the third-stage cooling part 13, and then fed to the downstream-side tank 2. The product liquid is not burned in the downstream-side conduit 11.

On the other hand, the interior of the second intermediate piping system 6, which is not used for sterilization of the product liquid, is subjected to the CIP for cleaning off the burnt product or impurities derived from the product liquid sterilized before the product liquid being handled now. The cleaning solution is fed under pressure by the cleaning solution pump 20 from the cleaning solution storage tank 19 of the CIP unit 14, and flows into the second intermediate piping system 6 through the second intermediate piping system inlet 17 coupled to the cleaning solution inlet 18. The cleaning solution having flowed through the second intermediate piping system 6 returns to the cleaning solution storage tank 19 through the cleaning solution outlet 25 coupled to the second intermediate piping system outlet 23. The cleaning solution is thus circulated. The burnt product or impurities removed from the interior of the second intermediate piping system 6 by the cleaning solution is removed by a filter provided at a midpoint in the cleaning solution outflow piping 21b. The cleaning solution contaminated as a result of the cleaning is appropriately discharged from the circulation system, and a fresh cleaning solution is appropriately added. The circulated cleaning solution may be heated by the second-stage heating part 9b. The cleaning effect is improved if the cleaning solution is heated. Alternatively, a heating unit may be provided on the cleaning solution inflow piping 21a or cleaning solution outflow piping 21b of the CIP unit 14 to heat the cleaning solution.

After it is determined that the CIP is completed, water is flowed in the second intermediate piping system 6 to remove the cleaning solution. After the CIP is completed, the second intermediate piping system 6 enters into a standby state until sterilization of another product liquid is started or until sterilization of the product liquid in the first intermediate piping system 5, which is being used to sterilize the product liquid, is stopped because of a failure such as burning of the product liquid.

Figure 3:
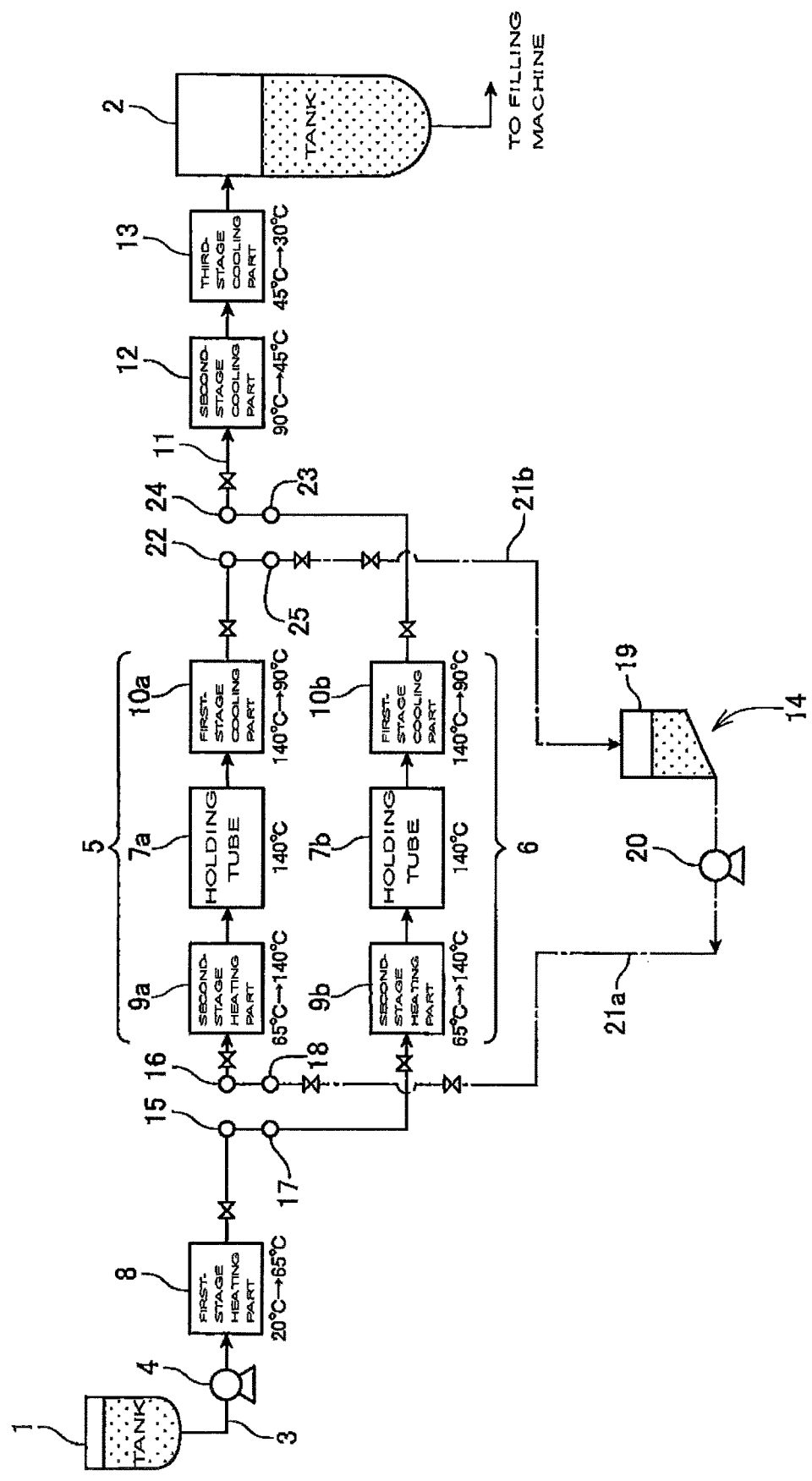
FIG. 3 is a block diagram showing the sterilization line according to the first embodiment of the present invention in which the interior of the one intermediate piping system is subjected to CIP while the other intermediate piping system is used to sterilize the product liquid.

When sterilization of the product liquid in the first intermediate piping system 5 is stopped in order to change the product liquid produced by the aseptic filling machine or because of a failure such as burning of the product liquid during sterilization, as shown in FIG. 3, the connections of the piping ends are changed to perform the CIP for the interior of the first intermediate piping system 5. Specifically, the product liquid inlet 15 and the second intermediate piping system inlet 17 are coupled to each other by the U-shaped pipe having been used to couple the product liquid inlet 15 and the first intermediate piping system inlet 16 to each other, and the cleaning solution inlet 18 and the first intermediate piping system inlet 16 are coupled to each other by the U-shaped pipe having been used to couple the second intermediate piping system inlet 17 and the cleaning solution inlet 18 to each other. Furthermore, the second intermediate piping system outlet 23 and the product liquid outlet 24 are coupled to each other by the U-shaped pipe having been used to couple the first intermediate piping system outlet 22 and the product liquid outlet 24 to each other, and the cleaning solution outlet 25 and the first intermediate piping system outlet 22 are coupled to each other by the U-shaped pipe having been used to couple the second intermediate piping system outlet 23 and the cleaning solution outlet 25 to each other. The flow path is changed by such coupling operations.

As shown in FIG. 3, by changing the flow path, a flow path for the product liquid is formed in which the product liquid flows from the upstream-side tank 1 to the downstream-side tank 2 through the upstream-side conduit 3, the second intermediate piping system 6 and then the downstream-side conduit 11. Before flowing the product liquid in the formed flow path for the product liquid, the CIP and the SIP are performed in succession or at the same time by circulating hot water from the upstream-side tank 1 through the upstream-side conduit 3, the second intermediate piping system 6 and the downstream-side conduit 11 by flowing water from the upstream-side tank 1, heating the water in the first-stage heating part 8, the second-stage heating part 9b and the holding tube 7b, flowing the heated water in the first-stage cooling part 10b, the second-stage cooling part 12 and the third-stage cooling part 13, and returning the heated water to the upstream-side tank 1 (not shown). The CIP and the SIP for the downstream-side tank 2 are performed in succession or at the same time through another system. After the SIP for the circulation path from the upstream-side tank 1 to the downstream-side conduit 11 through the upstream-side conduit 3 and the second intermediate piping system 6 and the SIP for the other circulation path system including the downstream-side tank are completed, the product liquid is flowed to the flow path for the product liquid shown in FIG. 3.

Second Embodiment

A second embodiment differs from the first embodiment in that the intermediate piping system in the standby state is not only subjected to the CIP but is subjected to the CIP and then to the SIP and further to a positive pressurization process. By entering into the standby state after performing the SIP and the positive pressurization process for the interior of the intermediate piping system, the SIP of the intermediate piping system, the downstream-side conduit 11 and the downstream-side tank 2 does not need to be performed after the flow path is changed, and another product liquid can be supplied immediately after the previous product liquid is discharged. Therefore, compared with the first embodiment, the switching time can be substantially reduced, and the productivity can be improved.

Figure 5:
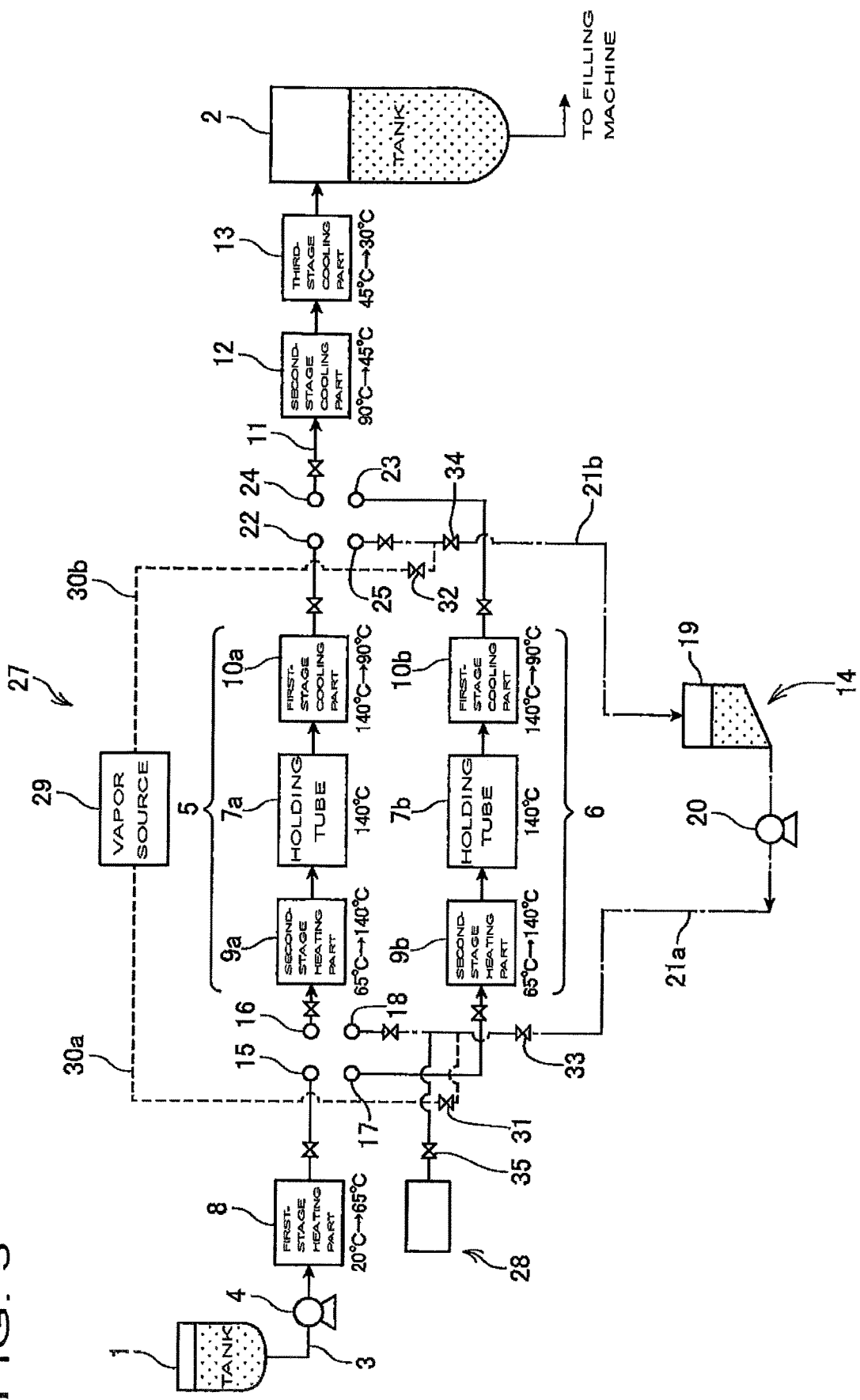
FIG. 5 is a block diagram showing a sterilization line according to a second embodiment of the present invention.

As shown in FIG. 5, a sterilization line according to the second embodiment is the sterilization line according to the first embodiment further provided with a SIP unit 27 that performs the SIP for sterilizing the interior of the intermediate piping system and a positive pressurization unit 28 that keeps the interior of the intermediate piping system at a positive pressure after the SIP.

The SIP unit 27 has a vapor source 29 that supplies steam at high temperature and high pressure, a vapor inflow conduit 30a that connects the vapor source 29 to the cleaning solution inflow piping 21a, and a vapor outflow conduit 30b that connects the vapor source 29 to the cleaning solution outflow piping 21b. The vapor inflow conduit 30a is provided with a vapor inflow valve 31, the vapor outflow conduit 30b is provided with a vapor outflow valve 32, the cleaning solution inflow piping 21a is provided with a cleaning solution inflow valve 33, and the cleaning solution outflow piping 21b is provided with a cleaning solution outflow valve 34.

The positive pressurization unit 28 is a unit that keeps the interior of the intermediate piping system at a positive pressure with aseptic air after the SIP in order to maintain the aseptic condition in the intermediate piping system sterilized by the SIP. More specifically, the positive pressurization unit 28 is a unit that feeds air from an air compressor or a blower after sterilizing the air through a aseptic filter. The positive pressurization unit 28 is connected to the cleaning solution inflow piping 21a and is provided with a positive pressurization valve 35.

Figure 6:
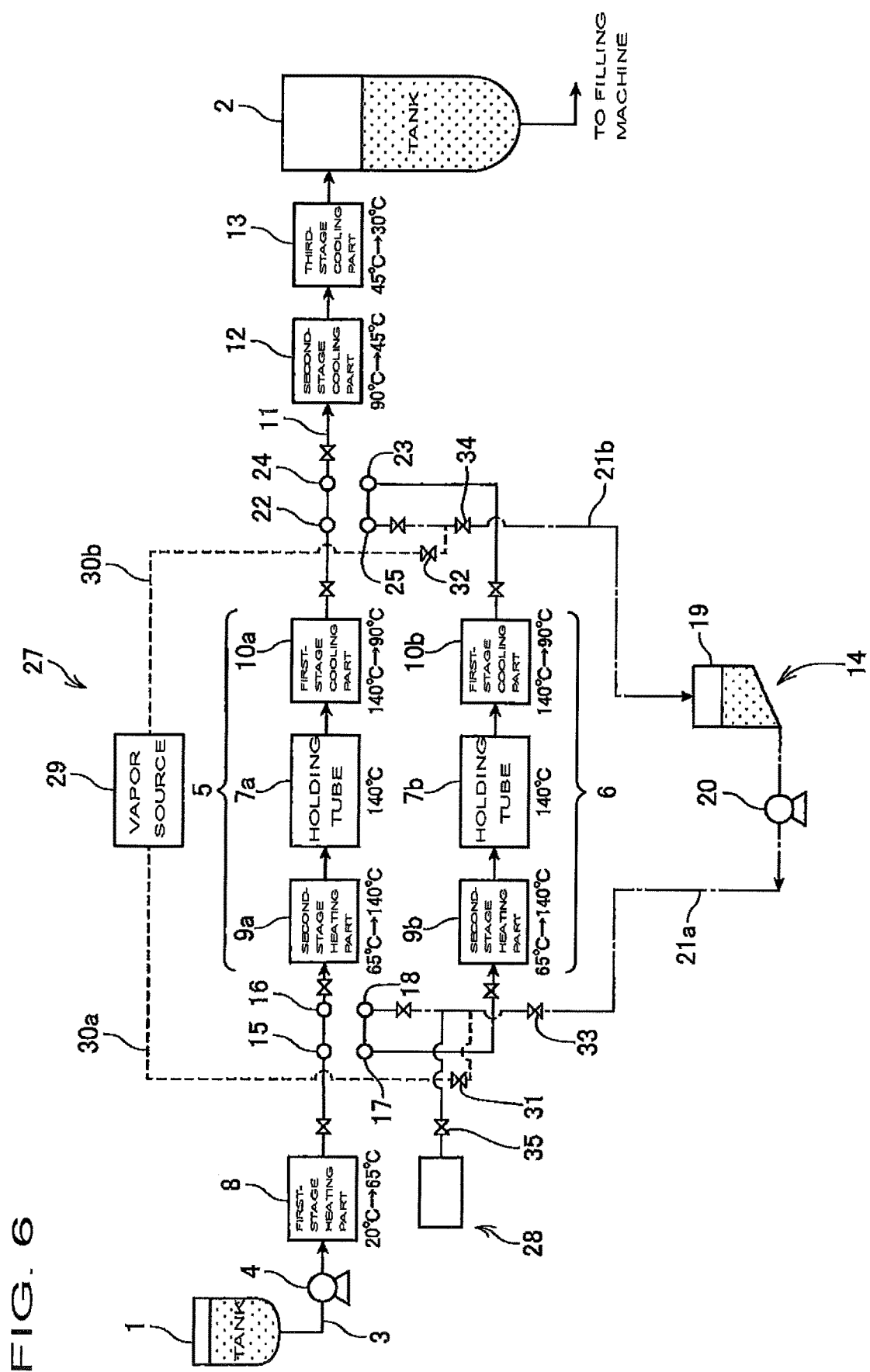
FIG. 6 is a block diagram showing the sterilization line according to the second embodiment of the present invention in which one intermediate piping system is used to sterilize a product while the interior of the other intermediate piping system is subjected to CIP, SIP, and a positive pressurization process.

As shown in FIG. 6, when the product liquid inlet 15 and the first intermediate piping system inlet 16 are coupled to each other, the second intermediate piping system inlet 17 and the cleaning solution inlet 18 are coupled to each other, the first intermediate piping system outlet 22 and the product liquid outlet 24 are coupled to each other, and the second intermediate piping system outlet 23 and the cleaning solution outlet 25 are coupled to each other, the product liquid flows in the first intermediate piping system 5, and the cleaning solution flows in the second intermediate piping system 6.

The product liquid is supplied from the upstream-side tank 1 through the upstream-side conduit 3, and is fed under pressure to the first-stage heating part 8 by the pump 4. The product liquid is further fed to the first intermediate piping system 5 through the product liquid inlet 15 and the first intermediate piping system inlet 16, flows to the downstream-side conduit 11 through the second-stage heating part 9a, the holding tube 7a, the first-stage cooling part 10a, the first intermediate piping system outlet 22 and the product liquid outlet 24, and is fed to the downstream-side tank 2 through the second-stage cooling part 12 and the third-stage cooling part 13.

On the other hand, the interior of the second intermediate piping system 6, which is not used for sterilization of the product liquid, is subjected to the CTP for cleaning off the burnt product or impurities derived from the product liquid sterilized before the product liquid being handled now. The cleaning solution is fed under pressure by the cleaning solution pump 20 from the cleaning solution storage tank 19 of the CIP unit 14, the cleaning solution inflow valve 33 is opened, and the cleaning solution flows into the second intermediate piping system 6 through the second intermediate piping system inlet 17 coupled to the cleaning solution inlet 18. The cleaning solution having flowed through the second intermediate piping system 6 returns to the cleaning solution storage tank 19 through the cleaning solution outlet 25 coupled to the second intermediate piping system outlet 23. The cleaning solution is thus circulated.

After it is determined that the CIP is completed, the SIP of the interior of the second intermediate piping system 6 is performed by feeding vapor into the second intermediate piping system 6 by closing the cleaning solution inflow valve 33 and the cleaning solution outflow valve 34 and opening the vapor inflow valve 31 and the vapor outflow valve 32. Although the SIP is performed using steam in FIG. 6, the SIP can also be performed using heated water. When steam or heated water at a predetermined temperature is flowed in the second intermediate piping system 6 for a predetermined time, the SIP of the interior of the second intermediate piping system after the CIP is completed. After the CIP is completed, the cleaning solution may be washed away by flowing water in the second intermediate piping system 6. The cleaning solution may be washed away by discharging the steam or heated water used in the SIP. In the SIP, the steam or heated water may be heated by the second-stage heating part 9b and the holding tube 7b, thereby reducing or omitting the external heating.

The SIP may be performed without using steam or heated water. Specifically, the SIP may be performed after the CIP or at the same time as the CIP by heating the cleaning solution used for the CIP to a temperature suitable for the SIP in the second-stage heating part 9b or a heating unit provided on the cleaning solution inflow piping 21a or cleaning solution outflow piping 21b and circulating the heated cleaning solution in the flow path formed by the intermediate piping system 6 and the CIP unit. When the SIP is performed using the cleaning solution flowing in a flow path including valves, the back of a valve seat of a valve providing a vapor barrier may be unable to be cleaned. However, with the flow path using the swing bend, a reduced number of valves is required, so that such a problem can be made less likely.

After it is determined that the SIP is completed, the interior of the second intermediate piping system 6 is kept at a positive pressure by closing the vapor inflow valve 31 and the vapor outflow valve 32 and opening the positive pressurization valve 35, thereby preventing bacteria or the like from entering the second intermediate piping system 6 from outside. The second intermediate piping system 6 enters into the standby state until sterilization of another product liquid is started or until sterilization of the product liquid in the first intermediate piping system 5 is stopped because of a failure such as burning of the product liquid.

When sterilization of the product liquid in the first intermediate piping system 5 is stopped in order to change the product liquid produced by the aseptic filling machine or because of a failure such as burning of the product liquid during sterilization, as shown in FIG. 7, the connections of the piping ends are changed to change the flow path. Specifically, the product liquid inlet 15 and the second intermediate piping system inlet 17 are coupled to each other by the U-shaped pipe having been used to couple the product liquid inlet 15 and the first intermediate piping system inlet 16 to each other, and the cleaning solution inlet 18 and the first intermediate piping system inlet 16 are coupled to each other by the U-shaped pipe having been used to couple the second intermediate piping system inlet 17 and the cleaning solution inlet 18 to each other. Furthermore, the second intermediate piping system outlet 23 and the product liquid outlet 24 are coupled to each other by the U-shaped pipe having been used to couple the first intermediate piping system outlet 22 and the product liquid outlet 24 to each other, and the cleaning solution outlet 25 and the first intermediate piping system outlet 22 are coupled to each other by the U-shaped pipe having been used to couple the second intermediate piping system outlet 23 and the cleaning solution outlet 25 to each other. The flow path is changed by such coupling operations.

If the flow path is exposed to outside air when the flow path is changed, the interior of the second intermediate piping system 6 in the standby state, which has been subjected to the SIP and kept aseptic, is contaminated with bacteria or the like. To avoid this, a chamber is provided which shields the swing bend panel 26 shown in FIG. 4 and the U-shaped pipes coupled to the piping ends in the swing bend panel 26 from outside air. The chamber is provided with a steam inlet and a steam outlet used to sterilize the interior of the chamber. The chamber is further provided with an aseptic air supply unit that maintains the aseptic condition in the chamber after the interior of the chamber is heated and sterilized with steam. The sterilization of the interior of the chamber may not be performed using steam but may be performed using a bactericide such as hydrogen peroxide.

Before the flow path is changed, the interior of the chamber is sterilized, and aseptic air is supplied into the chamber. Then, the flow path is changed while the aseptic condition in the chamber is maintained. The change of the flow path may be manually performed by providing a glove in the chamber. Alternatively, if two U-shaped pipes are connected to a shaft, which can be rotated by a rotational air actuator, in such a manner that the U-shaped pipes can be press-fitted to and separated from the openings of the swing bend panel 26 with an air motor, the flow path can be mechanically changed.

After the flow path is changed, the product liquid flows from the upstream-side tank 1 to the downstream-side tank 2 through the upstream-side conduit 3, the second intermediate piping system 6 and the downstream-side conduit 11. The cleaning solution used for the CIP is circulated from the cleaning solution storage tank 19 through the first intermediate piping system 5. Since the SIP of the interior of the second intermediate piping system 6 is completed, sterilization of another product liquid can be immediately started by discharging the previous product liquid from the upstream-side conduit 3, the downstream-side conduit 11, and the downstream-side tank 2. Therefore, the time required to change the product liquid can be substantially reduced.

Although the present invention is configured as described above, the present invention is not limited to the embodiments described above. For example, the method of heating and cooling the product liquid is not limited to the method using the shell-and-tube heat exchangers but can be a method using plate heat exchangers. Alternatively, an injection system or an infusion system may be used. Furthermore, the number of the parallel intermediate piping systems is not limited to two but can be increased.

REFERENCE SIGNS LIST 1 upstream-side tank
2 downstream-side tank
5 first intermediate piping system
6 second intermediate piping system
14 CIP unit
26 swing bend panel
27 SIP unit
28 positive pressurization unit

The invention claimed is:

1. A cleaning method for a sterilization line, the sterilization line including a conduit through which a product liquid is transferred, the conduit being provided with one or more stages of heating parts that sterilize the product liquid, and one or more stages of cooling parts that cool the product liquid from the one or more stages of the heating parts in a stepwise manner, wherein the sterilization line includes a plurality of parallel intermediate piping systems in a section thereof from the one or more stages of the heating parts that lies in a temperature range in which the product liquid can be burned to the one or more stages of the cooling parts that lies in a temperature range in which the product liquid can be burned, wherein the section includes at least one of the one or more stages of the heating part that lies in the temperature range in which the product liquid can be burned, and wherein cleaning in place (CIP) of the plurality of parallel intermediate piping systems is performed by switching between the plurality of parallel intermediate piping systems, where switching between a flow path of the product liquid and a flow path of a cleaning solution used for the CIP upstream of the plurality of parallel intermediate piping systems and switching between the flow path of the product liquid and the flow path of the cleaning solution used for the CIP downstream of the plurality of parallel intermediate piping systems are achieved by a swing bend.

2. The cleaning method for a sterilization line according to claim 1, wherein an intermediate piping system is subjected to sterilizing in place (SIP) after or at the same time as the CIP and is further subjected to a positive pressurization process.

3. The cleaning method for a sterilization line according to claim 2, wherein the swing bend is provided in a shielded chamber, wherein an interior of the shielded chamber is sterilized to provide a sterilized shielded chamber before the switching between the flow paths, and wherein the switching between the flow paths is performed while maintaining an aseptic condition in the sterilized shielded chamber.

* * * * *